(12) United States Patent
Shelso

(10) Patent No.: US 7,867,268 B2
(45) Date of Patent: Jan. 11, 2011

(54) STENT DELIVERY SYSTEM FOR SELF-EXPANDING STENT

(75) Inventor: Susan I. Shelso, Plymouth, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 54 days.

(21) Appl. No.: 10/670,405

(22) Filed: Sep. 24, 2003

(65) Prior Publication Data

US 2005/0065590 A1 Mar. 24, 2005

(51) Int. Cl.
*A61F 2/06* (2006.01)
(52) U.S. Cl. ...................... 623/1.11; 604/104
(58) Field of Classification Search ................. 606/108, 606/198; 604/164.01, 104, 523, 534, 535; 623/1.11
See application file for complete search history.

(56) References Cited

U.S. PATENT DOCUMENTS

| | | | |
|---|---|---|---|
| 4,016,864 A * | 4/1977 | Sielaff et al. ................. | 600/364 |
| 4,913,141 A | 4/1990 | Hillstead | |
| 4,950,227 A | 8/1990 | Savin et al. | |
| 5,026,377 A * | 6/1991 | Burton et al. ................ | 606/108 |
| 5,201,757 A * | 4/1993 | Heyn et al. .................. | 606/198 |
| 5,484,444 A | 1/1996 | Braunschweiler et al. | |
| 5,534,007 A | 7/1996 | St. Germain et al. | |
| 5,571,168 A | 11/1996 | Toro | |
| 5,634,928 A * | 6/1997 | Fischell et al. .............. | 623/1.11 |
| 5,662,703 A | 9/1997 | Yurek et al. | |
| 5,702,418 A * | 12/1997 | Ravenscroft ................ | 623/1.11 |
| 5,733,267 A | 3/1998 | Del Toro | |
| 5,759,186 A | 6/1998 | Bachmann et al. | |
| 5,772,669 A | 6/1998 | Vrba | |
| 5,776,142 A * | 7/1998 | Gunderson .................. | 623/1.11 |
| 5,800,517 A | 9/1998 | Anderson et al. | |
| 5,906,619 A | 5/1999 | Olson et al. | |
| 5,968,052 A | 10/1999 | Sullivan, III et al. | |
| 5,984,964 A * | 11/1999 | Roberts et al. .............. | 623/1.11 |
| 6,004,328 A | 12/1999 | Solar | |
| 6,019,778 A | 2/2000 | Wilson et al. | |
| 6,093,194 A | 7/2000 | Mikus et al. | |
| 6,113,608 A | 9/2000 | Monroe et al. | |

(Continued)

FOREIGN PATENT DOCUMENTS

EP 1 251 796 A 10/2002

OTHER PUBLICATIONS

International Search Report from PCT/US2004/021863.

(Continued)

*Primary Examiner*—Nicholas D Lucchesi
*Assistant Examiner*—Laura A Bouchelle
(74) *Attorney, Agent, or Firm*—Seager, Tufte & Wickhem, LLC

(57) ABSTRACT

A delivery device for a catheter-sheath assembly includes an outer shaft having proximal and distal ends, an inner shaft having proximal and distal ends, and a rigid inner member disposed within the inner shaft. A catheter is secured to the rigid inner member and a sheath extends from the outer shaft, covering the catheter and a stent maintained on the distal end of the catheter. The outer shaft is directable from a first position to a second position to retract the distal end of the sheath with respect to the catheter to deploy a stent or other therapeutic or corrective element from within the sheath.

10 Claims, 7 Drawing Sheets

U.S. PATENT DOCUMENTS

| | | |
|---|---|---|
| 6,120,522 A | 9/2000 | Vrba et al. |
| 6,159,228 A * | 12/2000 | Frid et al. .................. 606/198 |
| 6,168,617 B1 | 1/2001 | Blaeser et al. |
| 6,176,843 B1 * | 1/2001 | DiCaprio et al. ......... 604/99.03 |
| 6,190,360 B1 | 2/2001 | Iancea et al. |
| 6,344,044 B1 | 2/2002 | Fulkerson et al. |
| 6,368,344 B1 | 4/2002 | Fitz |
| 6,375,676 B1 | 4/2002 | Cox |
| 6,383,211 B1 | 5/2002 | Staehle |
| 6,425,898 B1 | 7/2002 | Wilson et al. |
| 6,447,522 B2 | 9/2002 | Gambale et al. |
| 6,527,779 B1 | 3/2003 | Rourke |
| 6,530,947 B1 | 3/2003 | Euteneuer et al. |
| 6,565,595 B1 | 5/2003 | DiCaprio et al. |
| 6,572,643 B1 | 6/2003 | Gharibadeh |
| 6,613,014 B1 | 9/2003 | Chi |
| 2003/0158594 A1 | 8/2003 | Kang et al. |

OTHER PUBLICATIONS

Written Opinion from PCT/US2004/021863.

* cited by examiner

US 7,867,268 B2

STENT DELIVERY SYSTEM FOR SELF-EXPANDING STENT

TECHNICAL FIELD

A system for treating a remote location within a patient is disclosed. More particularly, a system for delivering a corrective or therapeutic appliance to a remote location within a vasculature system is disclosed and which includes ergonomic handles, a catheter, and a sheath.

BACKGROUND OF THE RELATED ART

Devices having a retractable sheath associated with a catheter are used to treat a variety of conditions using endoluminal methods instead of open surgical procedures. For example, angioplasty and stent implantation procedures are often used to treat atherosclerotic disease or other occlusive conditions in blood vessels, such as the coronary and carotid arteries. During angioplasty, a catheter having an uninflated balloon on its distal end is percutaneously introduced into a patient's vasculature and advanced to a target treatment location, such as a stenosis within a blood vessel. Once the balloon is properly placed across the stenosis, the balloon is inflated to enlarge the lumen or vessel at the location of the stenosis. The balloon is then deflated, the inflation/deflation procedure may be repeated, and then the catheter is withdrawn from the patient's body.

To help prevent arterial closure, repair dissection, or prevent subsequent restenosis, a physician can implant an intravascular prosthesis, or a stent, for maintaining vascular patency inside the artery at the lesion. The stent may either be a self-expanding stent or a balloon expandable stent. For the latter type, the stent is often delivered on a balloon and the balloon is used to the expand the stent. Self-expanding stents may be made of shape memory materials such as nitinol or constructed of conventional metals but of a design which exhibits self expansion characteristics.

In certain known stent delivery catheters, a stent and an optional balloon are positioned at the distal end of the catheter, around a core lumen. The stent and balloon are held down and covered by a sheath or sleeve. When the distal portion is in its desired location of the targeted vessel, the sheath or sleeve is retracted to expose the stent. After the sheath is removed, the stent is free to self-expand or be expanded with a balloon.

For control of the sheath during deployment, several procedures have been proposed. The user may simply pull the proximal end of the sheath while holding the catheter in a fixed position. This, however, may not easily provide precise control of the retraction of the sheath.

To provide improved control, handle devices have been proposed which include a wheel and screw mechanism. A wheel extending around the circumference of the handle is coupled to a screw mechanism engaging the sheath and the catheter. As the wheel is rotated about the longitudinal axis of the handle, the screw mechanism moves the sheath axially with respect to the catheter.

With such devices, however, it may be difficult to remember which direction, i.e., clockwise or counterclockwise, is appropriate either to retract or advance the sheath with respect to the catheter. This may be particularly important when immediate action is necessary because of a complication during a procedure. In addition, these screw-type devices may be complicated, including many parts which may be difficult to assemble and/or expensive to make.

Another device has provided large handles to improve the ease and accuracy with which a stent can be delivered. However, as the French size of the device is reduced, the moving parts of the interior may not provide support for the catheter during the retraction procedure.

Accordingly, there is a need for an improved, intuitive, simple and safe device for controlling catheter-sheath systems.

SUMMARY OF THE DISCLOSURE

The disclosed device is directed to an apparatus for treating a remote location within the vasculature of a patient. The apparatus comprises an outer shaft, and inner shaft disposed within the outer shaft, and a rigid inner member disposed within the inner shaft. The outer shaft, inner shaft, and rigid inner member each have a proximal end and a distal end. The rigid inner member is fixedly attached or connected at its proximal end to the proximal end of the inner shaft and extends the length of the inner shaft. The outer shaft is slidable relative to the inner shaft from a first position in which the proximal end of the outer shaft is remote from the proximal end of the inner shaft to a second position in which the proximal end of the outer shaft is adjacent to the proximal end of the inner shaft.

DESCRIPTION OF THE PRESENTLY PREFERRED EMBODIMENTS

Figure 1:
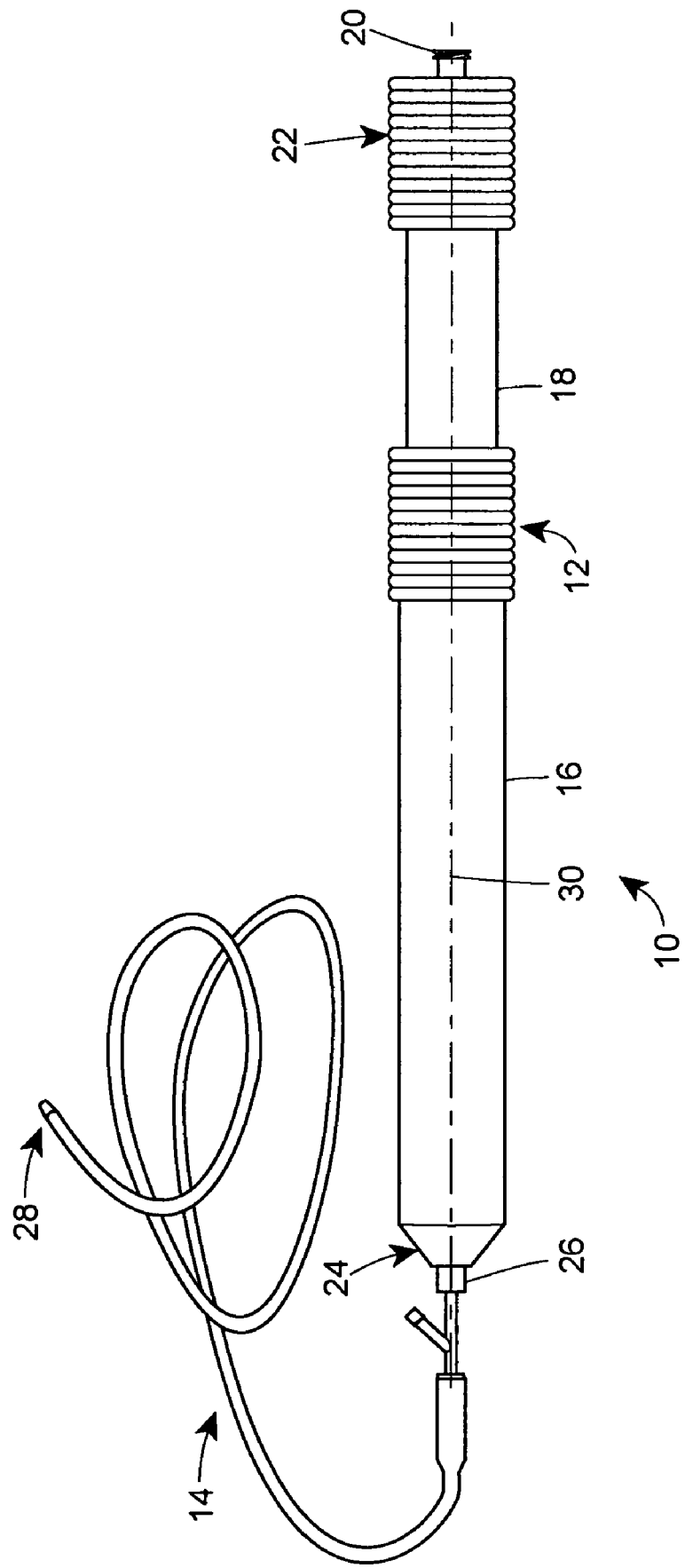
FIG. 1 is a side view of a stent delivery device constructed in accordance with the teachings of this disclosure.
Figure 11:
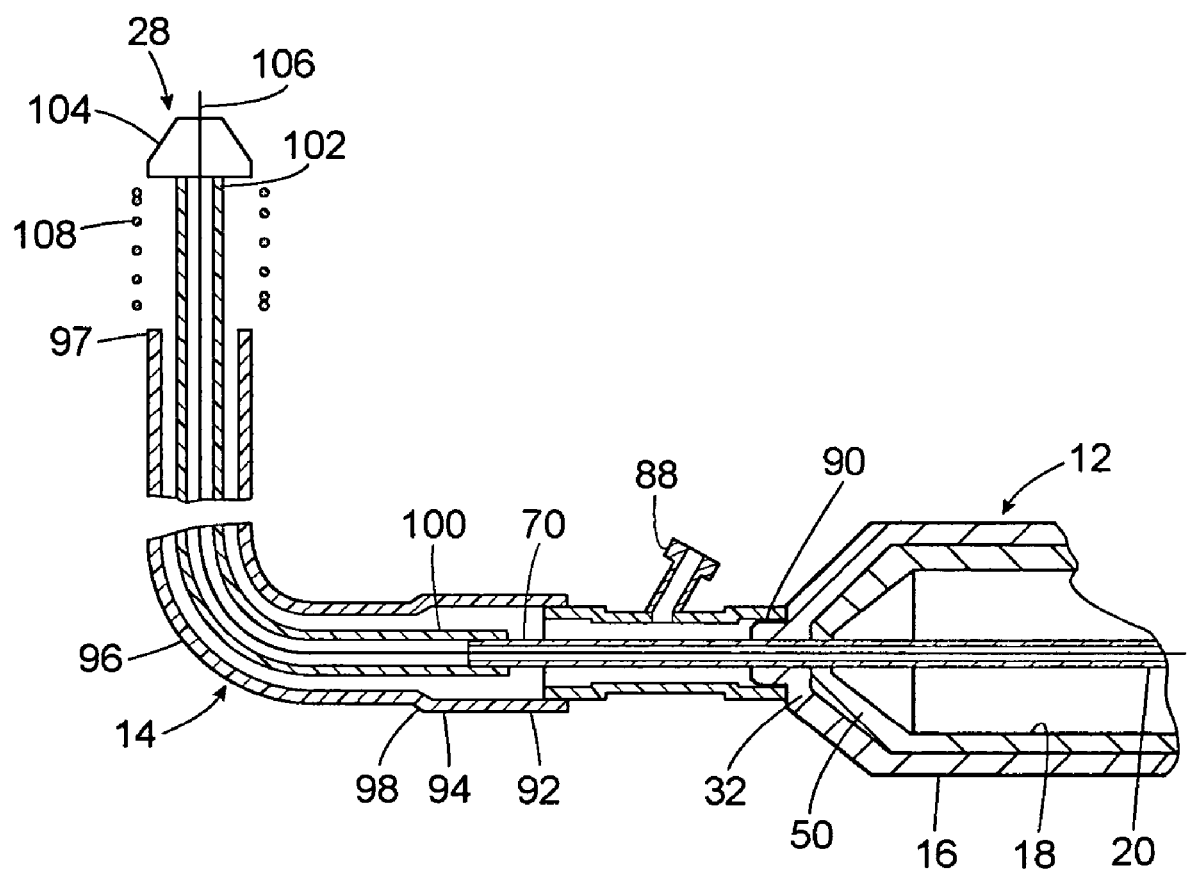
FIG. 11 is a fragmentary cross sectional view of the tube section of the stent delivery device, with the device in the second or deploy position.

Referring now to the drawings, FIG. 1 shows a stent delivery device generally depicted as reference number 10. The stent delivery device 10 includes a handle section 12 and a tube section 14. The handle section 12 includes an outer shaft 16, an inner shaft 18, and a rigid inner member 20. The outer shaft 16 and inner shaft 18 are slidable with respect to each other from a first or unretracted position, as shown in FIG. 1, to a second or deploy position, as shown in FIG. 11. The handle section 12 includes a proximal end 22 and a distal end 24. The proximal end 22 of the handle section 12 is also the proximal end 22 of the stent delivery device 10. The outer shaft 16 and inner shaft 18 define a common longitudinal axis 30.

The tube section 14 is configured to be inserted into the vasculature of a patient to safely dispose a treatment element at a predetermined location. The tube section 14 includes a proximal end 26 and a distal end 28. The proximal end 26 of the tube section 14 is adjacent to the distal end 24 of the handle section 12. The distal end 28 of the tube section 14 can also be the distal end 28 of the stent delivery device 10.

Figure 2:
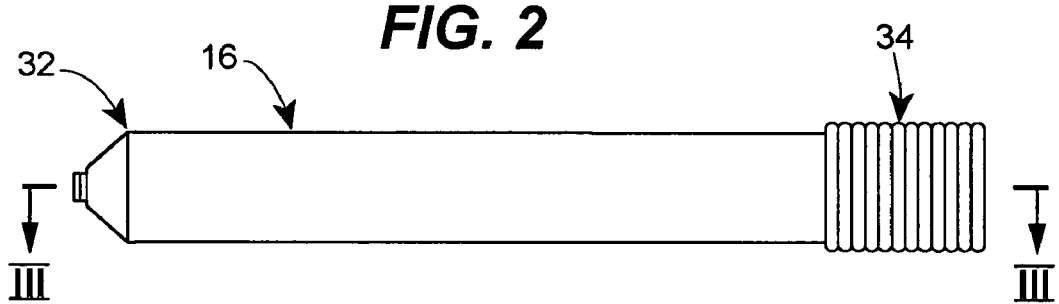
FIG. 2 is a side view of the outer shaft of the device of FIG. 1.
Figure 3:
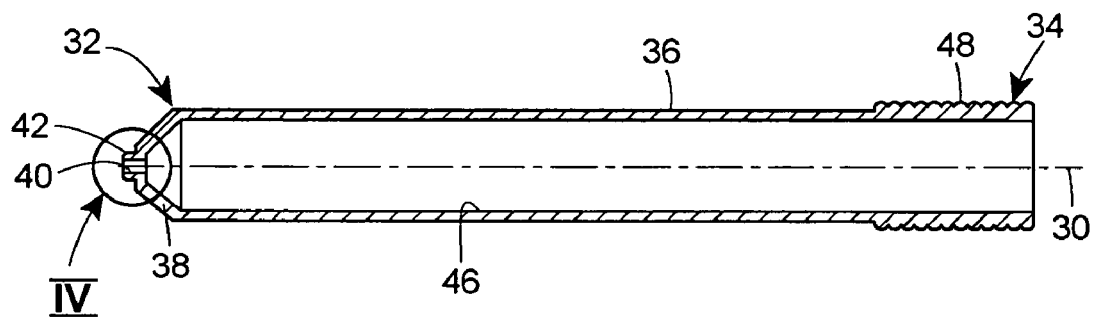
FIG. 3 is a cross sectional view of the outer shaft as shown in FIG. 2, taken along Line III-III in FIG. 2.
Figure 4:
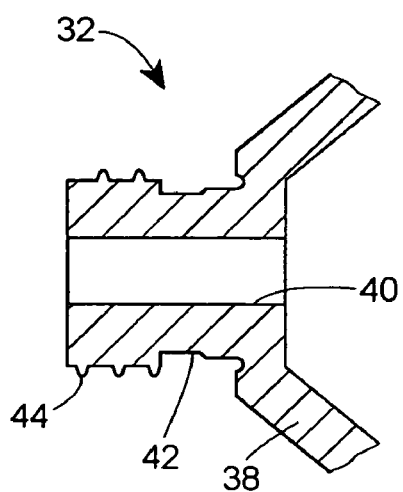
FIG. 4 is an enlarged cross sectional view of the distal end of the outer shaft shown in FIGS. 2 and 3 but further including a locking portion, taken substantially along Circle IV in FIG. 3.

Referring now to FIGS. 2-4, the outer shaft 16 of the handle section 12 is depicted. The outer shaft 16 has a distal end 32 and a proximal end 34. The outer shaft 16 has a generally elongate portion 36 which, in this example, is also circular in cross section. The elongate portion 36 terminates on the distal end 32 in a frusto-conical section 38, which has an aperture 40 that can coincide with the longitudinal axis 30. As best seen in FIG. 4, a lip 42 surrounds the aperture 40 and extends out from the frusto-conical section 38 of the outer shaft 16. In the present example, threads 44 are disposed on the lip 42 to allow for an item to be secured to the outer shaft. A threaded fitting found useful is commonly known in the art as a luer-lock type fitting.

The elongate portion 36 also defines an inner surface 46 on the inside of the outer shaft 16. The inner surface 46 provides a guideway for the inner shaft 18 to slide, as will be described herein. The elongate portion 36 terminates on its proximal end 34 in the grip 48. The grip 48 can include a plurality of raised annular rings, as shown, or any other device to facilitate the frictional holding and operation of the delivery device 10. The outer shaft 16 can be molded from plastic, or may be machined from a metal such as stainless steel, or manufactured in other suitable ways.

Figure 5:
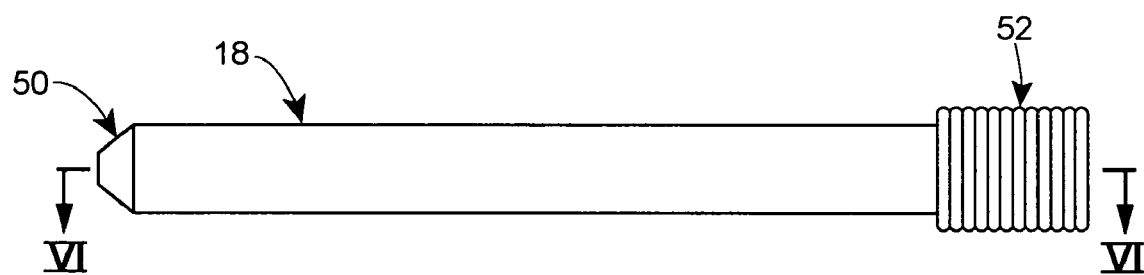
FIG. 5 is a side view of the inner shaft of the device of FIG. 1.
Figure 6:
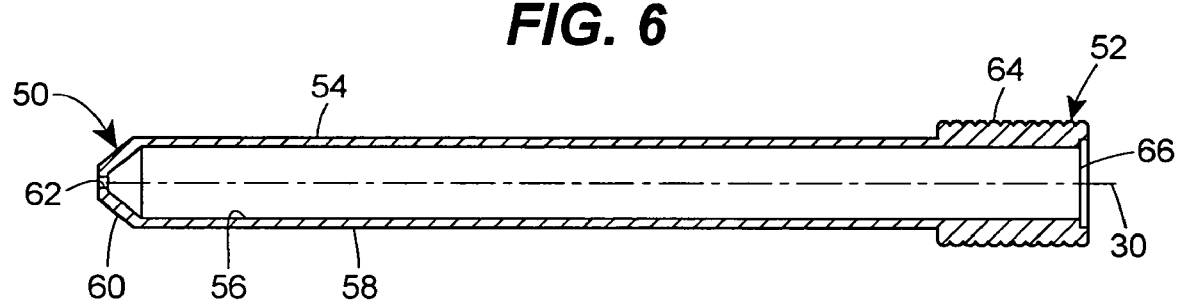
FIG. 6 is a cross sectional view of the inner shaft shown in FIG. 5, taken along Line VI-VI in FIG. 5.

FIGS. 5 and 6 illustrate the inner shaft 18. The inner shaft 18 has a distal end 50 and a proximal end 52. The inner shaft 14 has a generally elongate portion 54, which in this example is circular in cross section with an interior passage 56 and an outer surface 58. The diameter of the outer surface 58 is similar to or slightly less than the diameter of the inner surface 46 of the outer shaft 16, so that the inner shaft 18 can slide within the outer shaft 16. On the distal end 50, the elongate portion 54 terminates in a frusto-conical section 60. The frusto-conical section 60 has an aperture 62 which in this example coincides with the longitudinal axis 30 and the aperture 40 of the outer shaft 16.

On the proximal end 52, the inner shaft 18 terminates in a grip 64, which can be similar to the grip of the outer shaft 16. Disposed within the grip 64 is a seat 66. The seat 66 can support the rigid inner member 20, as will be described herein. In this example, the outer shaft 16 and the inner shaft 18 are cylindrical, with the inner shaft 18 disposed concentrically inside the outer shaft 16.

Figure 7:
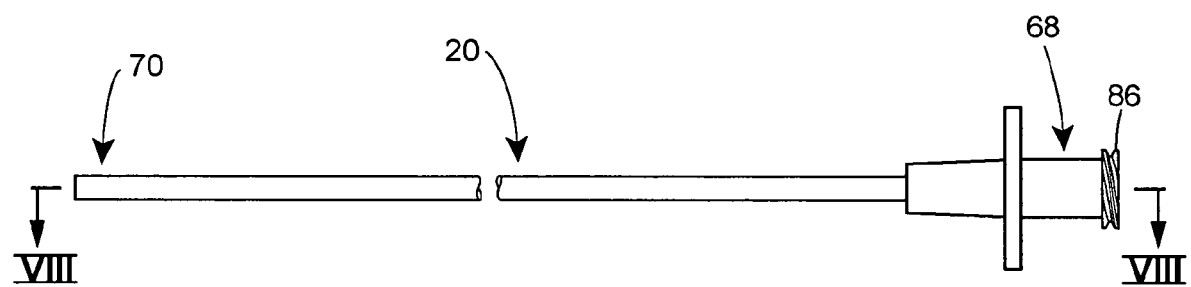
FIG. 7 is a side view of the rigid inner member of the device shown in FIG. 1.
Figure 8:
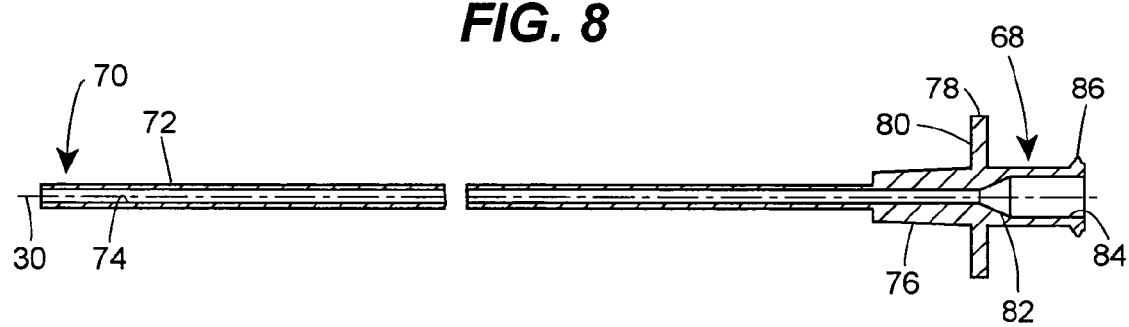
FIG. 8 is a cross sectional view of the rigid inner member shown in FIG. 7, taken along Line VIII-VIII in FIG. 7.

The rigid inner member 20 is disclosed in FIGS. 7 and 8. The rigid inner member 20 includes a proximal end 68 and a distal end 70. The rigid inner member 20 includes a narrow tubular elongate portion 72, defining a lumen 74 inside, which can be coincident with the longitudinal axis 30. On the proximal end 68, the walls of the elongate portion 72 thicken into a cylinder 76. Disposed on the cylinder 76 is a flange 78 with a mounting surface 80. Inside the cylinder 76, the lumen 74 widens via an interior conical section 82 into an enlarged axial passage 84. On the end of the cylinder 76 and the proximal end 68 is a threaded portion 86. The physician may attach a syringe (not shown) to the threaded portion 86 to flush the entire lumen 74 and the tube section 14 to ensure that no air or contaminents enter the patient's vasculature.

Figure 9:
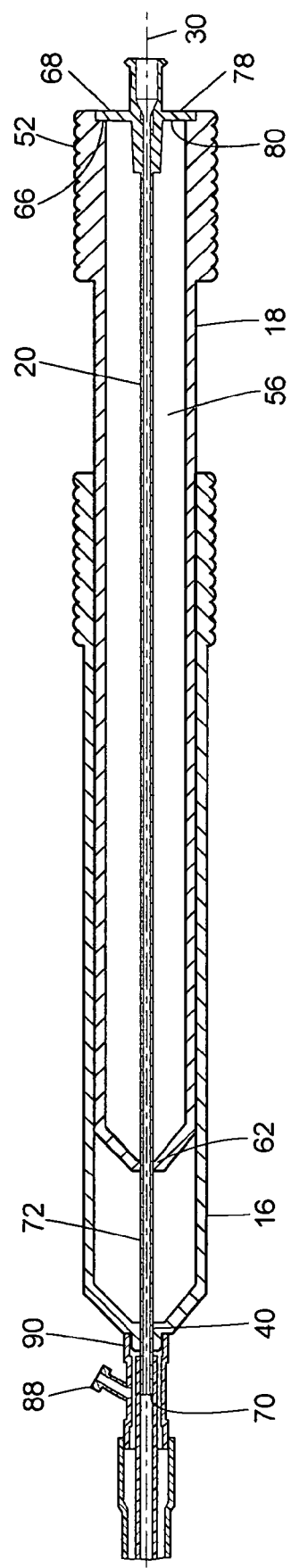
FIG. 9 is a fragmentary cross sectional view of the handle section of the stent delivery device of FIG. 1 in the first or unretracted position.

As seen in FIG. 9, the rigid inner member 20 is disposed within the interior passage 56 of the inner shaft 18 with the proximal end 68 of the rigid inner member 20 mounted to the proximal end 52 of the inner shaft 18. The mounting surface 80 of the flange 78 is fixed to the seat 66 of the inner shaft 18, with, in this example, the distal end 70 of the rigid inner member 20 extending through the aperture 62 of the inner shaft 18. Although in the disclosed example the elongate portion 72 extends through the aperture 40 of the outer shaft 16, it is also possible that the elongate portion 72 terminates at the aperture 62 of the inner shaft 18. As such, in the present example, the rigid inner member 20 has interior portion inside the inner shaft 18, and an exterior portion distal from the end of the outer shaft 16.

Figure 10:
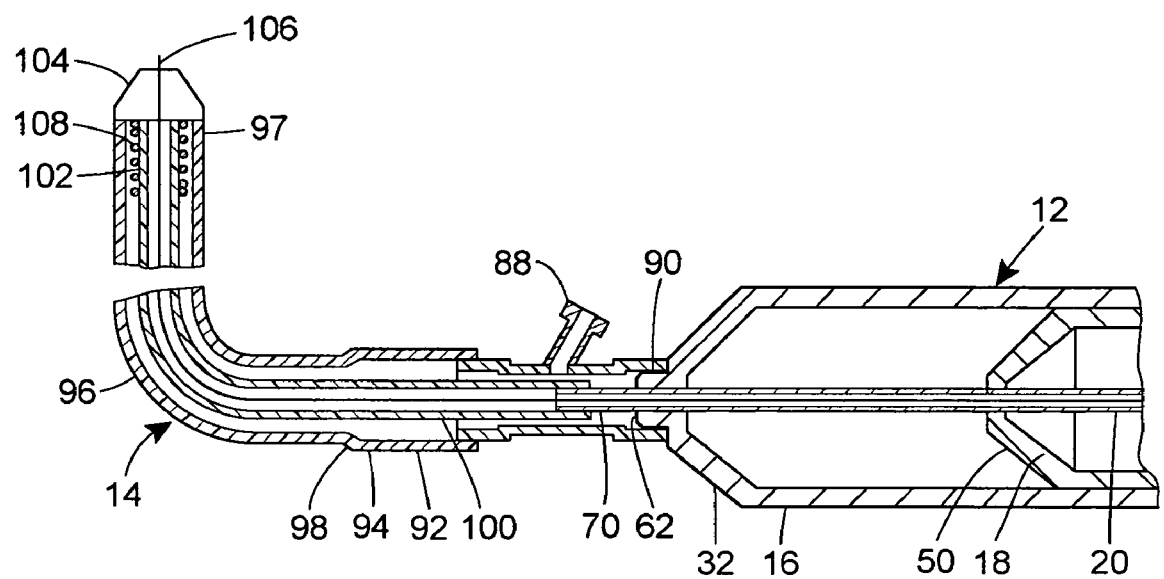
FIG. 10 is a fragmentary cross sectional view of the tube section of the stent delivery device, with the device in the first unretracted position.

Referring now to FIG. 10, the tube section 14 of the stent delivery device 10 is depicted in the first position. The tube section 14 can include a flush valve 88 connected to the lip 62 of the outer shaft 16. The flush valve 88 may be any standard valve known in the art to introduce liquid into the system to purge any pockets of air, including a Y-adapter valve, as shown in FIG. 1. A hemostatic seal 90 is disposed between the flush valve 88 and the handle section 12 to ensure that no air or contaminents from the handle section 12 are introduced into the tube section 14.

Attached to the flush valve 88 is a stepped outer tube 92. The stepped outer tube 92 includes a wide end 94 and a sheath 96 which are joined at a conical section 98. The wide end 94 is sized to fully encase the distal end 70 of the rigid inner member 20 when the delivery device 10 is in the second position. Attached to and extending away from the distal end 70 of the rigid inner member 20 is a catheter 100 that has a distal end 102. The catheter 100 is long narrow tube sized to fit within a blood vessel and reach a destination targeted for treatment within the body. Attached to the distal end 102 of the catheter 100 is a distal tip 104, which aids is sliding the tube section 14 through the patient. The catheter 100 may further be designed to accommodate and slide over a guide wire 106. The guide wire 106 can be inserted into the patient to the targeted location and guide the tube section 14 as it is moved to the targeted location by sliding over the guide wire 106.

As is best seen in FIGS. 1 and 10, the sheath 96 is a long tube which encloses the catheter 100. The length of the sheath 96 is configured such that a distal end 97 of the sheath 96 is proximate the distal end 102 of the catheter 100 when the device 10 is in the first position. Disposed on the distal end 102 of the catheter 100 is a treatment element 108 such as a self-expanding stent. The treatment element 108 is covered by the sheath 96 when the device is in the first position (see FIG. 10).

Referring now to FIG. 11, the stent delivery device 10 is depicted in the second position or the deploy position. In this drawing, the outer shaft 16 and the inner shaft 18 have been slid together relative to one another such that the distal end 32 of the outer shaft 16 has been pulled back to the distal end 50 of the inner shaft 18. Accordingly, the distal end 97 of the sheath 96 has been pulled away from the distal end 102 of the catheter 100 such that the treatment element 108 is uncovered and allowed to expand within the blood vessel of the patient.

In operation, with the stent delivery device 10 in the first position, the guide wire 106 is directed through the patient's vasculature by the physician to the desired location. The tube section 14 of the stent delivery device 10, including the catheter 100, the sheath 96, and the distal tip 104, is then fed over the guide wire 106 through the patient's vasculature, until the distal end 28 of the tube section 14 and the treatment device 108, in this example a self-expanding stent, have arrived at the desired location. The sheath 96 is disposed over the stent 108 and catheter 100 such that the stent 108 is in a collapsed state.

In the first position, in which the sheath 96 covers the stent 108, the relative position of the outer shaft 16 and inner shaft 18 is such that distal end 32 of the outer shaft 16 and the distal end 50 of the inner shaft 18 are remote from each other. To deliver the stent 108 to the desired location in the vasculature system, the user simply pulls the outer shaft 16 relative to the inner shaft 18 such that the respective distal ends 32 and 50 are brought together to a second position (shown in FIG. 11). The outer shaft 16 is directly connected to the sheath 96 through the stepped outer tube 92 and the locking structure at the lip 42. By pulling the outer shaft 16 relative to the inner shaft 18, the sheath 96 is pulled back from the distal tip 104, thus uncovering the self-expanding stent 108 and allowing the stent 108 to expand within the blood vessel, thereby helping to expand and support the blood vessel.

The position of the catheter 100, and consequently the stent 108, is maintained due to its connection to the inner shaft 18 by way of the rigid inner member 20. Instead of attempting to secure the relatively small catheter 100 directly to the large, easy-to-handle body of the inner shaft 18, the catheter 100 can be connected to the distal end 70 of the rigid inner member 20 and, in turn, the proximal end 68 of the rigid inner member 20 is connected to the inner shaft 18.

Further, instead of attempting to secure the relatively small sheath 96 directly to the large easy-to-handle outer shaft 16, the connection between the sheath 96 and the outer shaft 16 is made through the stepped outer tube 92. As a result, the stent delivery device 10 is easy to use, reliable, and provides the physician with an enhanced feel.

In a second example not shown, the sheath 96 may have a comparatively short length (for example, less than two inches), and a long tube may be connected to the sheath 96. In this example, the long tube has an interior diameter similar to or slightly less than the outer diameter of the sheath 96. The long tube may be attached to the sheath 96 in any way appreciated in the art, including bonding with adhesive, welding, or a tight frictional fit. In a further example (not shown), the wide end 94 and the sheath 92 of the stepped outer tube 90 may be two pieces of tubing that are bonded together. In these examples, the wide end 94 and the sheath 92 could be manufactured from different materials.

Numerous modifications and alternative embodiments will be apparent to those skilled in the art in view of the foregoing description. Accordingly, this description is to be construed as illustrative only. The details of the structure may be varied substantially without departing from the spirit and scope of the disclosure, and the exclusive use of all modifications which come within the scope of the appended claims is reserved.

I claim:

1. A treatment element delivery device, comprising:
    an outer shaft comprising a tapered distal end, a proximal end, and a lumen therebetween;
    an inner shaft slidably disposed within and concentric with the outer shaft, comprising a proximal end and a tapered distal end configured to engage the outer shaft distal end, wherein the outer shaft distal end is positioned distal to the inner shaft distal end, and the outer shaft is slidable relative to the inner shaft between a first position in which the distal end of the inner shaft is positioned within the lumen of the outer shaft and spaced from the distal end of the outer shaft and a second position in which the distal end of the inner shaft matingly engages the distal end of the outer shaft;
    a rigid inner member having distal and proximal ends and an interior portion disposed inside the inner shaft and defining a lumen within the inner shaft, the proximal end of the rigid inner member being coupled to the proximal end of the inner shaft, the rigid inner member further comprising an exterior portion protruding beyond the distal end of the inner shaft;
    a stepped exterior tube comprising a wide diameter end and a sheath, the wide diameter end being rigidly coupled to the distal end of the outer shaft and fully enclosing the exterior portion of the rigid inner member in the second position; and
    a catheter coupled to and extending distally from the rigid inner member distal end,
    the distal end of the catheter comprising a mounting region for a treatment element, said treatment element mounting region being covered by the distal end of the sheath in the first position, and the treatment element mounting region being uncovered by the distal end of the sheath in the second position.

2. The apparatus of claim 1, further comprising gripping portions disposed on the inner shaft and outer shaft.

3. The apparatus of claim 1, the sheath further comprising distal and proximal ends, and being directly movable by movement of the outer shaft from the first position to the second position.

4. The apparatus of claim 3, in which the catheter includes a distal end disposed adjacent the distal end of the sheath.

5. The apparatus of claim 4, wherein the distal end of the catheter is covered by the distal end of the sheath in the first position, and the distal end of the catheter is uncovered by the distal end of the sheath in the second position.

6. The apparatus of claim 5, further comprising a stent disposed on the distal end of the catheter.

7. The apparatus of claim 6, wherein the stent is deployed when the distal end of the sheath uncovers the distal end of the catheter by movement of the outer shaft from the first position to the second position.

8. The apparatus of claim 1, further comprising a valve to flush air from the sheath.

9. A treatment element delivery device, comprising:
    an outer shaft comprising distal and proximal ends and a lumen therebetween, wherein the distal end includes a tapered inner surface;
    an inner shaft slidably disposed within and concentric with outer shaft, comprising a proximal end and a distal end having a tapered outer surface configured to matingly engage the tapered inner surface of the outer shaft distal end, wherein the outer shaft distal end is positioned distal to the inner shaft distal end, and the outer shaft is slidable relative to the inner shaft between a first position in which the distal end of the inner shaft is positioned within the lumen of the outer shaft and spaced from the distal end of the outer shaft and a second position in which the tapered outer surface of the distal end of the inner shaft matingly engages the tapered inner surface of the distal end of the outer shaft;
    a rigid inner member having distal and proximal ends and an interior portion disposed inside the inner shaft and defining a lumen within the inner shaft, the proximal end of the rigid inner member being coupled to the proximal end of the inner shaft, the rigid inner member further comprising an exterior portion protruding beyond the distal end of the inner shaft;

a stepped exterior tube, comprising a wide diameter end and a sheath, the wide diameter end being rigidly coupled to the distal end of the outer shaft and fully enclosing the exterior portion of the rigid inner member in the second position;

the sheath having distal and proximal ends, and being directly movable by movement of the outer shaft from the first position to the second position;

a catheter, comprising a distal end and a proximal end, the proximal end of the catheter being coupled to and extending distally from the rigid inner member, the distal end of the catheter being disposed adjacent the distal end of the sheath, the distal end of the catheter being covered by the distal end of the sheath in the first position, and the distal end of the catheter being uncovered by the distal end of the sheath in the second position; and a stent disposed on the distal end of the catheter, wherein the stent is deployed when the distal end of the sheath uncovers the distal end of the catheter by movement of the outer shaft from the first position to the second position.

10. A method of deploying a treatment element, comprising:

providing an outer shaft comprising distal and proximal ends and a lumen therebetween;

providing an inner shaft comprising distal and proximal ends, slidably disposed within and concentric with the outer shaft, comprising a proximal end and a distal end configured to engage the outer shaft distal end, wherein the outer shaft distal end is positioned distal to the inner shaft distal end;

providing a rigid inner member comprising distal and proximal ends, the rigid inner member further comprising an interior portion disposed inside the inner shaft and defining a lumen within the inner shaft, the proximal end of the rigid inner member being directly mounted to the proximal end of the inner shaft, the rigid inner member further comprising an exterior portion protruding beyond the distal end of the inner shaft;

providing a catheter comprising a proximal end and a distal end, the proximal end of the catheter being rigidly coupled to and extending distally from the rigid inner member and the distal end comprising a treatment element mounting region;

providing a stepped exterior tube comprising a wide diameter end and a sheath, the wide diameter end being rigidly coupled to the distal end of the outer shaft and fully enclosing the exterior portion of the rigid inner member in the second position, the sheath comprising a proximal end and a distal end, the proximal end being fixedly connected to the distal end of the outer shaft, the distal end being disposed proximate the distal end of the catheter; and uncovering the treatment element mounting region at the distal end of the catheter from the distal end of the sheath by moving the outer shaft from a first position in which the inner shaft is positioned within the lumen of the outer shaft and the proximal end of the outer shaft is spaced from the proximal end of the inner shaft to a second position in which the proximal end of the outer shaft engages the proximal end of the inner shaft.

* * * * *